US011961233B2

(12) United States Patent
Liu

(10) Patent No.: US 11,961,233 B2
(45) Date of Patent: Apr. 16, 2024

(54) METHOD AND APPARATUS FOR TRAINING IMAGE SEGMENTATION MODEL, COMPUTER DEVICE, AND STORAGE MEDIUM

(71) Applicant: Tencent Technology (Shenzhen) Company Limited, Shenzhen (CN)

(72) Inventor: Luyan Liu, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 342 days.

(21) Appl. No.: 17/470,433

(22) Filed: Sep. 9, 2021

(65) Prior Publication Data

US 2021/0407086 A1 Dec. 30, 2021

Related U.S. Application Data

(63) Continuation of application No. PCT/CN2020/091455, filed on May 21, 2020.

(30) Foreign Application Priority Data

May 27, 2019 (CN) .......................... 201910448095.6

(51) Int. Cl.
G06T 7/00 (2017.01)
G06T 7/11 (2017.01)
G06T 7/162 (2017.01)

(52) U.S. Cl.
CPC .............. *G06T 7/0012* (2013.01); *G06T 7/11* (2017.01); *G06T 7/162* (2017.01);
(Continued)

(58) Field of Classification Search
CPC ......... G06T 7/0012; G06T 7/11; G06T 7/162; G06T 7/00; G06T 2207/30096;
(Continued)

(56) References Cited

U.S. PATENT DOCUMENTS

2017/0270671 A1* 9/2017 Garnavi ................. G06T 7/187
2018/0137623 A1* 5/2018 Stålring .................... G06T 7/11
(Continued)

FOREIGN PATENT DOCUMENTS

CN 108062753 A 5/2018
CN 108389210 A 8/2018
(Continued)

OTHER PUBLICATIONS

Extended European Search Report for European Patent Application No. 20815327.0 dated Jun. 23, 2022, 10 pages.
(Continued)

*Primary Examiner* — Tuan H Nguyen
(74) *Attorney, Agent, or Firm* — Crowell & Moring LLP

(57) ABSTRACT

This application provides a method and apparatus for training an image segmentation model, a device, and a storage medium. The method includes: training an initial image segmentation model by using source domain samples, to obtain a pre-trained image segmentation model; extracting a predicted segmentation result of a source domain image and a predicted segmentation result of a target domain image by using the pre-trained image segmentation model; training a first discriminator by using the predicted segmentation result of the source domain image and the predicted segmentation result of the target domain image; training a second discriminator by using the predicted segmentation result of the source domain image and a standard segmentation result of the source domain image; and iteratively training the pre-trained image segmentation model according to a loss function of the pre-trained image segmentation model, an adversarial loss function of the first discriminator, and an adversarial loss function of the second discriminator, until convergence, to obtain a trained image segmentation model.

20 Claims, 6 Drawing Sheets

(52) U.S. Cl.
CPC .............. *G06T 2207/20072* (2013.01); *G06T 2207/20081* (2013.01); *G06T 2207/20084* (2013.01); *G06T 2207/30096* (2013.01)

(58) Field of Classification Search
CPC . G06T 2207/20081; G06T 2207/20084; G06T 2207/20072
See application file for complete search history.

(56) References Cited

U.S. PATENT DOCUMENTS

| | | |
|---|---|---|
| 2019/0066281 A1 | 2/2019 | Zheng et al. |
| 2019/0147582 A1 | 5/2019 | Lee et al. |

FOREIGN PATENT DOCUMENTS

| | | |
|---|---|---|
| CN | 109101975 A | 12/2018 |
| CN | 109166126 A | 1/2019 |
| CN | 109190707 A | 1/2019 |
| CN | 109241972 A | 1/2019 |
| CN | 109299716 A | 2/2019 |
| CN | 109543502 A | 3/2019 |
| CN | 109558901 A | 4/2019 |
| CN | 110148142 A | 8/2019 |

OTHER PUBLICATIONS

Arnab Kumar Mondal et al: "Few-shot 3D Multi-modal Medical Image Segmentation using Generative Adversarial Learning", arxiv. org, Cornell University Library, 201 Olin Library Cornell University Ithaca, NY 14853, Oct. 29, 2018, XP80932951.

Xue et al: "SegAN: Adversarial Network with Muti-scale L Loss for Medical Image Segmentation", ARXIV E-PRINTS, Jun. 1, 2017 (Jun. 1, 2017), XP002793294.

International Search Report and Written Opinion with English Translation of International Patent Application No. PCT/CN2020/091455 dated Aug. 4, 2020; 12 pages.

Office Action for Chinese Patent Application No. 201910448095.6 dated Sep. 13, 2022, 38 pages.

Yongfei Pu, "Remote Sensing Image Classification and Segmentation Based on Convolutional Neural Network", Journal/Magazine: China Excellent Thesis for Master's Degree—Complete Database, issue 1, Jan. 15, 2019, 60 pages.

Arnab Kumar Mondal et al., "Few-shot 3D Multi-modal Medical Image Segmentation using Generative Adversarial Learning", arXiv:1810.12241v1, Oct. 29, 2018, 10 pages.

Yi-Hsuan Tsai et al., "Learning to Adapt Structured Output Space for Semantic Segmentation", arXiv:1802.10349v3, Feb. 28, 2018, 11 pages.

Liang Yan et al., "Adversarial Domain Adaptation with a Domain Similarity Discriminator for Semantic Segmentation of Urban Areas", Sep. 6, 2018, 6 pages.

\* cited by examiner (a) (b) (c) (d) (e) (f)

METHOD AND APPARATUS FOR TRAINING IMAGE SEGMENTATION MODEL, COMPUTER DEVICE, AND STORAGE MEDIUM

RELATED APPLICATION

This application is a continuation application of the International PCT Application No. PCT/CN2020/091455, filed with the China National Intellectual Property Administration, PRC on May 21, 2020 which claims priority to Chinese Patent Application No. 201910448095.6, filed with the China National Intellectual Property Administration, PRC on May 27, 2019, each of which is incorporated herein by reference in their entireties.

FIELD OF THE TECHNOLOGY

Embodiments of this disclosure relate to the field of image recognition technologies, and in particular, to a method and apparatus for training an image segmentation model, a computer device, and a storage medium.

BACKGROUND OF THE DISCLOSURE

Image segmentation refers to classifying pixels in an image and marking a target region. Image segmentation may be applied to fields such as medical image analysis, unmanned driving, a geographic information system, and underwater object detection. For example, in the field of medical image analysis, image segmentation may be used for implementing tasks such as positioning of tumors and other lesions, measurement of tissue volume, and study of an anatomical structure.

A conventional image segmentation method depends on a large number of marked images, and an assumption of this method is that data distribution of a training image set (that is, a source domain image) and a test image set (that is, a target domain image) are consistent. However, in a practical application, complex and diverse image data distribution is difficult to meet this assumption. As a result, a generalization capability of a model trained on a specific image set is poor, and test performance on image sets from different domains or image sets with domain changes is greatly reduced.

In the related art, in a process of training an image segmentation model, a source domain image and a target domain image are aligned in a feature space, so that a model finally obtained through training may be suitable for the target domain image in the feature space. However, an image transmitted from the feature space to an output space is further processed in a plurality of steps, resulting in an insufficient accuracy of an image segmentation result of the target domain image outputted from the output space.

SUMMARY

According to various embodiments of this disclosure, a method and apparatus for training an image segmentation model, a computer device and a storage medium are provided.

A method for training an image segmentation model is provided, performed by a computer device, the method including:

training an initial image segmentation model by using source domain samples, to obtain a pre-trained image segmentation model, the source domain samples including a source domain image and a standard segmentation result of the source domain image;

extracting a predicted segmentation result of the source domain image and a predicted segmentation result of a target domain image by using the pre-trained image segmentation model;

training a first discriminator by using the predicted segmentation result of the source domain image and the predicted segmentation result of the target domain image, the first discriminator being used for discriminating whether an inputted segmentation result is from a source domain or a target domain;

training a second discriminator by using the predicted segmentation result of the source domain image and the standard segmentation result of the source domain image, the second discriminator being used for discriminating whether an inputted segmentation result is the predicted segmentation result or the standard segmentation result; and retraining the pre-trained image segmentation model according to a loss function of the pre-trained image segmentation model, an adversarial loss function of the first discriminator, and an adversarial loss function of the second discriminator, such iterative loop training being performed until converging to obtain a trained image segmentation model.

An image segmentation method is provided, performed by a computer device, the method including:

obtaining a to-be-segmented image from a target domain;

processing the to-be-segmented image by invoking a trained image segmentation model, to obtain a segmentation result of the to-be-segmented image, the trained image segmentation model being obtained by training an image segmentation model through adversarial learning in an output space by using a first discriminator and a second discriminator, the first discriminator being used for reducing a difference between a predicted segmentation result of a target domain image and a predicted segmentation result of a source domain image in a process of training the image segmentation model, and the second discriminator being used for reducing a difference between the predicted segmentation result of the source domain image and a standard segmentation result of the source domain image in the process of training the image segmentation model.

An apparatus for training an image segmentation model is provided, the apparatus including:

a first training module, configured to train an initial image segmentation model by using source domain samples, to obtain a pre-trained image segmentation model, the source domain samples including a source domain image and a standard segmentation result of the source domain image;

a result extraction module, configured to extract a predicted segmentation result of the source domain image and a predicted segmentation result of a target domain image by using the pre-trained image segmentation model;

a second training module, configured to train a first discriminator by using the predicted segmentation result of the source domain image and the predicted segmentation result of the target domain image, the first discriminator being used for discriminating whether an inputted segmentation result is from a source domain or a target domain;

a third training module, configured to train a second discriminator by using the predicted segmentation result of the source domain image and the standard segmentation result of the source domain image, the second discriminator being used for discriminating whether an inputted segmentation result is the predicted segmentation result or the standard segmentation result; and a fourth training module, configured to retrain the pre-trained image segmentation model according to a loss function of the pre-trained image segmentation model, an adversarial loss function of the first discriminator, and an adversarial loss function of the second discriminator, such iterative loop training being performed until converging to obtain a trained image segmentation model.

A computer device includes a processor and a memory, the memory storing at least one instruction, at least one segment of program, a code set or an instruction set, the at least one instruction, the at least one segment of program, the code set or the instruction set being loaded and executed by the processor to implement the method for training an image segmentation model or implement the image segmentation method.

A non-transitory computer-readable storage medium is provided, storing at least one instruction, at least one program, a code set, or an instruction set, and the at least one instruction, the at least one program, the code set, or the instruction set being loaded and executed by a processor to implement the method for training an image segmentation model or implement the image segmentation method.

A computer program product is provided, the computer program product, when executed, being configured to perform the method for training an image segmentation model or implement the image segmentation method.

Details of one or more embodiments of this disclosure are provided in the subsequent accompanying drawings and descriptions. Other features and advantages of this application become obvious with reference to the specification, the accompanying drawings, and the claims.

DESCRIPTION OF EMBODIMENTS

Figure 1:
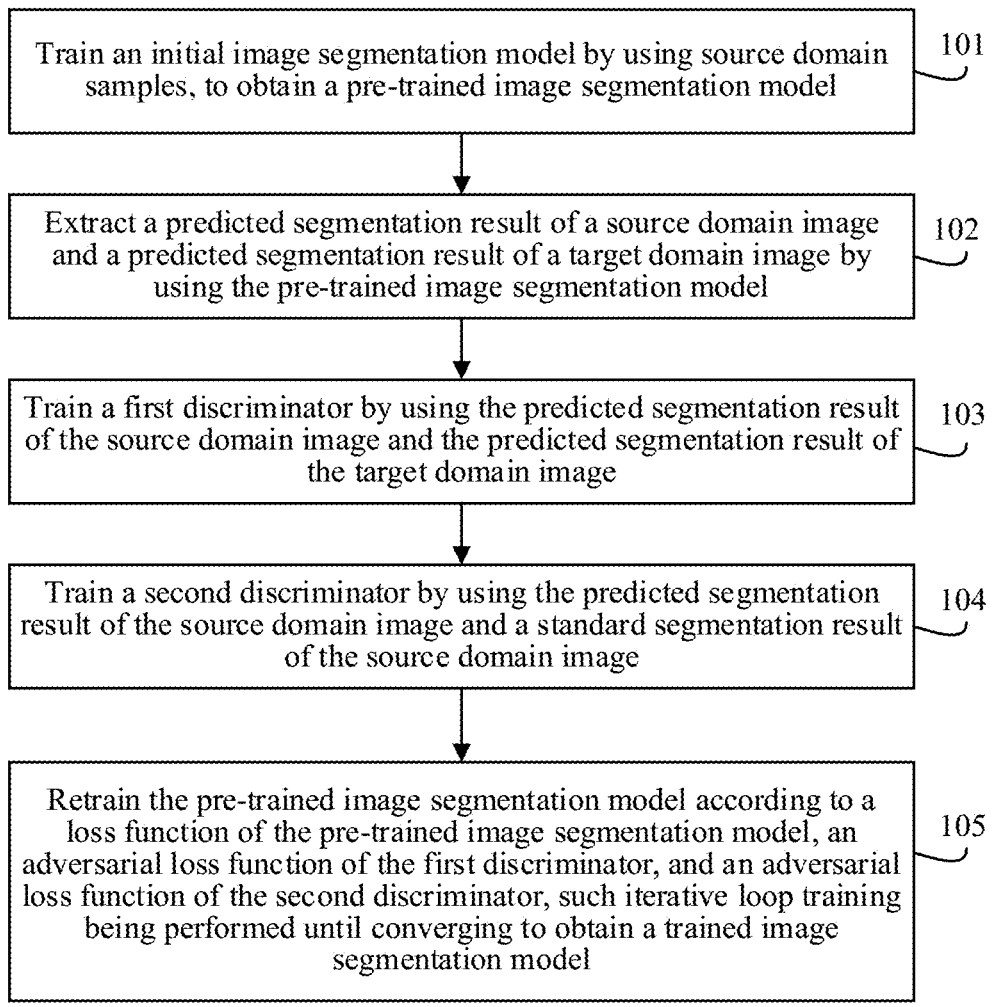
FIG. 1 is a flowchart of a method for training an image segmentation model according to an embodiment of this disclosure.

To make the objectives, technical solutions, and advantages of this application clearer, the following further describes implementations of this application in detail with reference to the accompanying drawings. It is to be understood that the specific embodiments described herein are merely used for explaining this application but are not intended to limit this application.

Image segmentation refers to classifying pixels in an image and marking a target region. Image segmentation may be applied to the fields such as medical image analysis, unmanned driving, a geographic information system, and underwater object detection. In the field of medical image analysis, image segmentation may be used for implementing positioning of a tumor and another lesion, measurement of tissue volume, study of an anatomical structure, and the like. In the field of unmanned driving, image segmentation may be used for processing an ambient image after an in-vehicle camera or a lidar obtains the ambient image, detecting a ground and recognizing a passable region, and then planning a driving path. In the field of the geographic information system, image segmentation may be used for processing a satellite remote sensing image after acquiring the satellite remote sensing image, recognizing a road, a river, crops, a building, and the like, and marking each pixel in the image.

In technical solutions provided in the embodiments of this disclosure, an image segmentation model that is domain adaptive in an output space is provided based on a deep convolutional neural network (DCNN) and an adversarial learning idea. Predicted segmentation results of a source domain image and a target domain image are extracted by using an image segmentation model pre-trained by using source domain samples. Further, the predicted segmentation results of the source domain image and the target domain image are inputted to a first discriminator, and the predicted segmentation result of the source domain image and a standard segmentation result of the source domain image are inputted to a second discriminator. Iterative loop training is performed on the pre-trained image segmentation model by using an adversarial learning idea until the model converges, to obtain a trained image segmentation model. In the technical solution provided in this disclosure, the source domain image and the target domain image are aligned in the output space, so that the trained image segmentation model can reduce, in the output space, a difference between the source domain image and the target domain image, and reduce an error in segmentation of a target domain by the trained image segmentation model, to further enable a segmentation result of the target domain image to be more accurate.

In the method provided in the embodiments of this disclosure, the steps may be performed by a computer device. The computer device includes an electronic device such as a personal computer (PC) or a server with data calculation, processing, and storage capabilities.

FIG. 1 is a flowchart of a method for training an image segmentation model according to an embodiment of this disclosure. The method is applied to a computer device and may include the following steps (101 to 105):

Step 101. Train an initial image segmentation model by using source domain samples, to obtain a pre-trained image segmentation model.

The source domain samples include a source domain image and a standard segmentation result of the source domain image. The source domain image may be an image acquired by an image acquisition device (for example, a camera, a medical device, or a lidar), or an image pre-stored locally, or an image obtained from a network, which is not limited in this embodiment of this disclosure. In addition, the source domain image may be an image in a picture format, or a video image. A format of the source domain image is not limited in this embodiment of this disclosure.

The source domain image includes a target region. The target region may be a region that a user is interested in, such as a character region, an animal region, a plant region, or another designated region in a landscape image; or may be a tissue organ region, a cell region, or a lesion region in a medical image, which is not limited in this embodiment of this disclosure.

The standard segmentation result of the source domain image refers to the source domain image with the target region being accurately marked, that is, a real segmentation label. The standard segmentation result may be manually marked by a professional person.

Using an example in which the source domain image is a medical image, the target region may be a lesion region in the medical image, and the standard segmentation result of the source domain image is a medical image with the lesion region in the medical image being accurately marked, which is beneficial to clinical diagnosis and treatment and medical research. For example, for a medical image of a specific part of a patient body, if there is a tumor region in the image, a clinician or other relevant personnel need to obtain a more accurate position of the tumor region for clinical diagnosis and treatment and medical research, and the tumor region is the target region of the medical image. The image segmentation model is configured to segment a target region from an image inputted to the image segmentation model, to obtain a segmentation result corresponding to the inputted image. The source domain samples include the source domain image and the standard segmentation result of the source domain image, and therefore the source domain samples can be used to train an initial image segmentation model and update relevant parameters of the initial image segmentation model, to obtain a pre-trained image segmentation model. Compared with the initial image segmentation model, the pre-trained image segmentation model has a more accurate segmentation result for the same image.

A frame structure of the image segmentation model may be a convolutional neural network (CNN), a deep CNN (DCNN), a residual network (ResNet), a densely connected convolutional network (DenseNet), or the like, or may be another model structure that may be used for image segmentation, which is not limited in this embodiment of this disclosure.

Step 102. Extract a predicted segmentation result of the source domain image and a predicted segmentation result of a target domain image by using the pre-trained image segmentation model.

The target domain image and the source domain image are images of the same type of tasks, but image data distributions are different. For example, in the field of medical image analysis, the target domain image and the source domain image are used for detecting a tumor region. However, the target domain image and the source domain image are from different acquisition devices, or from different hospitals or different centers, resulting in great differences in the distributions of the target domain image and the source domain image. In another example, the target domain image is a computed tomography (CT) image, and the source domain image is a magnetic resonance imaging (MRI) image. Because the two different medical images focus on expressing different information, distributions of the tumor region in the CT image and the MRI image are different. In another example, in the field of unmanned driving, the target domain image and the source domain image are both used for identifying a ground and recognizing a passable region. However, the target domain image is acquired by using an in-vehicle camera, and the source domain image is acquired by using a lidar. Because images acquired by different devices are represented in different forms, there are differences in the ground and the passable region.

Using a medical image as an example, the medical image has a plurality of modalities such as an MRI, a CT, a positron emission computed tomography (PET), and a proton density (PD) weighted image, and therefore the distribution of the same region in medical images of different modalities changes to some extent. This is referred to as a domain change phenomenon. Similarly, when acquired medical images are from different imaging devices (e.g., imaging devices from different vendors) of different hospitals (or centers), data distributions of the medical images with the same modality may also be quite different. This is also a domain change phenomenon. The target domain image and the source domain image may both be used for segmenting a brain tumor tissue region. However, the target domain image and the source domain image are medical images from different centers or different hospitals, that is, distributions of tumor regions in the target domain image and the source domain image may be different.

The predicted segmentation result of the source domain image refers to an image with the target region in the source domain image being accurately marked by using the image segmentation model. The predicted segmentation result of the target domain image refers to an image with the target region in the target domain image being accurately marked by using the image segmentation model.

After a computer device inputs the source domain image and the target domain image to the pre-trained image segmentation model, the image segmentation model may obtain respective feature maps of the source domain image and the target domain image, and mark category information to which each pixel in the feature map pertains, to mark the target region, that is, to obtain a predicted segmentation result of the image. Still using an example in which the tumor region is segmented from the medical image, the image segmentation model needs to distinguish whether a pixel in the image pertains to the tumor region, and mark the pixel pertaining to the tumor region, to obtain an image with the tumor region being segmented.

Step 103. Train a first discriminator by using the predicted segmentation result of the source domain image and the predicted segmentation result of the target domain image.

After extracting the predicted segmentation result of the source domain image and the predicted segmentation result of the target domain image, the computer device inputs the segmentation results to the first discriminator, to train the first discriminator. The first discriminator is used for discriminating whether the inputted segmentation result is from a source domain or a target domain. By training the first discriminator, the trained first discriminator can discriminate as accurately as possible whether the inputted segmentation result is from the source domain or the target domain.

In some embodiments, the discriminator may be constructed by using CNNs. For example, the CNNs may include a plurality of convolution layers. For example, the CNNs include five convolution layers, and each convolution layer has a convolution kernel size of 2, stride of 2, and padding of 1. In addition, each of the first four layers may be followed by an activation function layer, and the activation function layer may include a leaky ReLU layer, a ReLU layer, a RReLU layer, or the like. An output of the last layer of the convolution layer is 2, which corresponds to a category of the inputted predicted segmentation result discriminated by the discriminator, for example, from the source domain and from the target domain.

Step 104. Train a second discriminator by using the predicted segmentation result of the source domain image and the standard segmentation result of the source domain image.

After extracting the predicted segmentation result of the source domain image, the computer device may further input the segmentation result and the standard segmentation result of the source domain image to the second discriminator, to train the second discriminator. The second discriminator is used for discriminating whether the inputted segmentation result is the predicted segmentation result or the standard segmentation result. By training the second discriminator, the trained second discriminator can discriminate as accurately as possible whether the inputted segmentation result is the predicted segmentation result or the standard segmentation result.

In some embodiments, the second discriminator may also be constructed by using CNNs. A structure of the second discriminator may be the same as or different from that of the first discriminator, which is not limited in this embodiment of this disclosure.

Step 105. Retrain the pre-trained image segmentation model according to a loss function of the pre-trained image segmentation model, an adversarial loss function of the first discriminator, and an adversarial loss function of the second discriminator, such iterative loop training being performed until converging to obtain a trained image segmentation model. The convergence of a model describes a progression towards a network state where the neural network has learned to properly respond to a set of training patterns within a margin of error. The margin of error may be pre-defined or pre-configured. In some embodiments, a convergence is reached when additional training will not improve the model.

The loss function of the pre-trained image segmentation model is used for measuring a segmentation accuracy of the image segmentation model.

The adversarial loss function of the first discriminator is used for measuring a difference degree between the predicted segmentation result of the target domain image and the predicted segmentation result of the source domain image. The predicted segmentation result of the target domain image and the predicted segmentation result of the source domain image are inputted to the first discriminator for adversarial learning. The first discriminator needs to discriminate as much as possible whether the inputted segmentation result is from the source domain or the target domain, while the image segmentation model needs to segment the target domain image as accurately as possible, so that the first discriminator discriminates the segmentation result of the target domain image as being from the source domain. Through such an adversarial learning process, the segmentation accuracy of the image segmentation model is improved.

The adversarial loss function of the second discriminator being used for measuring a difference degree between the predicted segmentation result of the source domain image and the standard segmentation result of the source domain image. The predicted segmentation result of the source domain image and the standard segmentation result of the source domain image are inputted to the second discriminator for adversarial learning. The second discriminator needs to discriminate as much as possible whether the inputted segmentation result is the predicted segmentation result or the standard segmentation result of the source domain image, while the image segmentation model needs to segment the source domain image as accurately as possible, so that the second discriminator discriminates the predicted segmentation result of the source domain image as the standard segmentation result. Through such an adversarial learning process, the difference between the predicted segmentation result of the source domain image and the standard segmentation result of the source domain image is reduced.

The computer device iteratively performs training on the pre-trained image segmentation model according to the loss function of the pre-trained image segmentation model, the adversarial loss function of the first discriminator, and the adversarial loss function of the second discriminator, until the model converges, to obtain a trained image segmentation model. The iterative training on the pre-trained image segmentation model includes repeating steps 102 to 105, to continuously adjust a parameter of the image segmentation model, according to a value of the loss function of the image segmentation model, a value of the adversarial loss function of the first discriminator, and a value of the adversarial loss function of the second discriminator that are obtained in each round (or iteration) of training, until the model converges, to obtain the trained image segmentation model. The trained image segmentation model can reduce a difference between the source domain image and the target domain image, and reduce an error in segmentation of a target domain by the trained image segmentation model, to further enable image visual information outputted by the target domain image in an output space to be more accurate.

Figure 2:
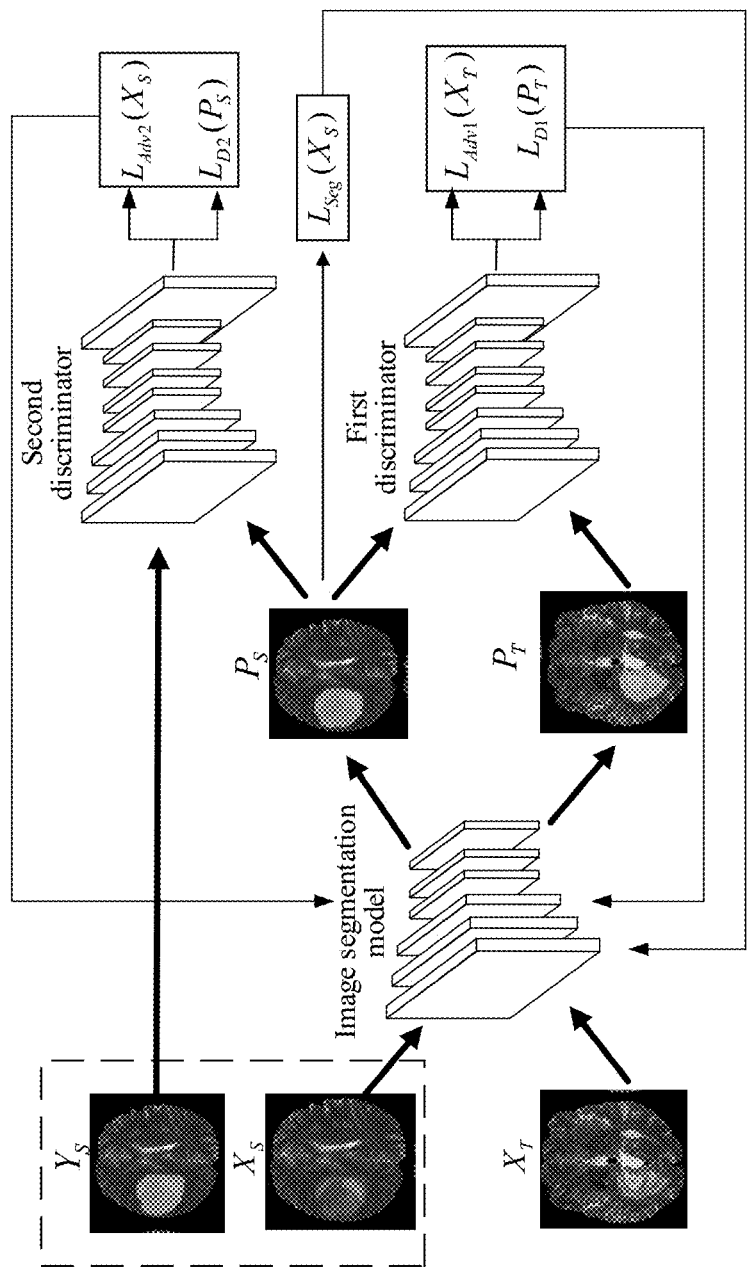
FIG. 2 is an exemplary schematic flowchart of a method for training an image segmentation model.

FIG. 2 is an exemplary flowchart of a method for training an image segmentation model. $X_S$ represents a source domain image, $Y_S$ represents a standard segmentation result of the source domain image, $X_T$ represents a target domain image, $P_S$ represents a segmentation result of the source domain image, $P_T$ represents a segmentation result of the target domain image, $L_{D1}(P_T)$ represents a discrimination loss function of a first discriminator, $L_{Adv1}(X_T)$ represents an adversarial loss function of the first discriminator, $L_{D2}(P_S)$ represents a discrimination loss function of a second discriminator, $L_{Adv2}(X_S)$ represents an adversarial loss function of the second discriminator, and $L_{Seg}(X_S)$ represents a loss function of a pre-trained image segmentation model.

As shown in FIG. 2, a computer device inputs the source domain image and the target domain image to an image segmentation model, the image segmentation model may be a pre-trained image segmentation model, to obtain a segmentation result of the source domain image and a segmentation result of the target domain image. The segmentation result of the source domain image and the segmentation result of the target domain image are inputted to the first discriminator, to obtain a discrimination result of the first discriminator, and further obtain the discrimination loss function and the adversarial loss function of the first discriminator. The segmentation result of the source domain image and the standard segmentation result of the source domain image are inputted to the second discriminator, to obtain a discrimination result of the second discriminator, and further obtain the discrimination loss function and the adversarial loss function of the second discriminator. Then, the loss function of the pre-trained image segmentation model, the adversarial loss function of the first discriminator, and the adversarial loss function of the second discriminator are fed back to the image segmentation model to adjust a parameter of the pre-trained image segmentation model by minimizing a value of the loss function of the pre-trained image segmentation model and a value of a weighted sum of the two adversarial loss functions and maximizing values of the discrimination loss function of the first discriminator and the discrimination loss function of the second discriminator, to obtain a trained image segmentation model. The trained image segmentation model can accurately segment an image from the target domain, and has good segmentation performance and generalization capabilities.

The technical solution provided in this embodiment of this disclosure is applicable to a model training process of an image segmentation task in the artificial intelligence (AI) field, and is particularly suitable for a process of training an image segmentation model by using a dataset with a domain change phenomenon in a training dataset. Using a segmentation task for medical images of different modalities as an example, the training dataset may include a plurality of medical images captured from different medical devices. In this application scenario, an input is a medical image, and an output is a segmentation result of segmenting a lesion region. An image segmentation network is optimized by using the first discriminator and the second discriminator. The segmentation result of the source domain image and the segmentation result of the target domain image predicted by the image segmentation model are as close as possible to the standard segmentation result of the source domain image. Finally, a more accurate image segmentation model is trained to assist a doctor in diagnosis and analysis of a lesion.

In summary, in the technical solution provided in this embodiment of this disclosure, predicted segmentation results of a source domain image and a target domain image are extracted by using an image segmentation model pre-trained by using source domain samples. Further, the predicted segmentation results of the source domain image and the target domain image are inputted to a first discriminator, and the predicted segmentation result of the source domain image and a standard segmentation result of the source domain image are inputted to a second discriminator. Iterative training is performed on the pre-trained image segmentation model by using an adversarial learning idea until the model converges, to obtain a trained image segmentation model. In the technical solution provided in this disclosure, the source domain image and the target domain image are aligned in the output space, so that the trained image segmentation model can reduce, in the output space, a difference between the source domain image and the target domain image, and reduce an error in segmentation of a target domain by of the trained image segmentation model, to further enable a segmentation result of the target domain image to be more accurate.

In addition, in this embodiment of this disclosure, based on the first discriminator, the image segmentation model is further trained by the second discriminator, so that the segmentation result of the source domain image and the segmentation result of the target domain image predicted by the image segmentation model are as close as possible to the standard segmentation result of the source domain image, thereby further improving precision of the model.

Figure 3:
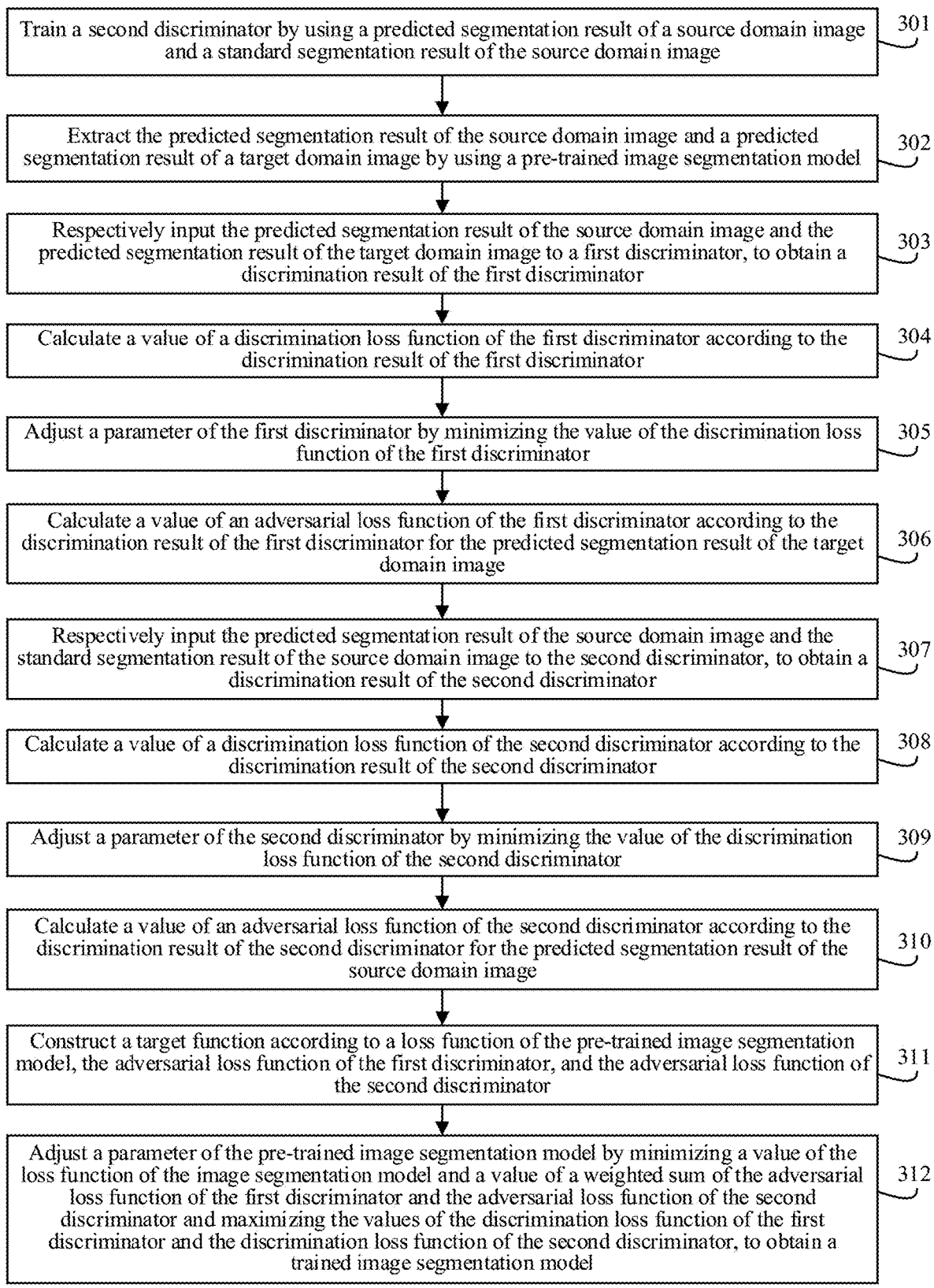
FIG. 3 is a flowchart of a method for training an image segmentation model according to another embodiment of this disclosure.

FIG. 3 is a flowchart of a method for training an image segmentation model according to another embodiment of this disclosure. The method may include the following steps (301 to 312):

Step 301. Train an initial image segmentation model by using source domain samples, to obtain a pre-trained image segmentation model.

The source domain samples include a source domain image and a standard segmentation result of the source domain image.

In this embodiment of this disclosure, the image segmentation model may be a DeepLabv3+ model. The DeepLabv3+ model includes an atrous spatial pyramid pooling (ASPP) module and an encoder-decoder structure and combines advantages of the ASPP module and the encoder-decoder structure. The ASPP can encode, at a plurality of different ratios and different receptive fields, texture information of different scales in data through a pooling operation, and the encoder-decoder structure can obtain clearer boundary information of an object by gradually restoring spatial information.

In some other embodiments, the image segmentation model may also be a DeepLabv2 model, a RefineNet model, or a ResNet model, which is not limited in this embodiment of this disclosure.

Step 302. Extract a predicted segmentation result of the source domain image and a predicted segmentation result of a target domain image by using the pre-trained image segmentation model.

In one implementation, after obtaining the pre-trained image segmentation model by using the source domain samples, the computer device inputs the source domain samples to the pre-trained image segmentation model again, to extract the predicted segmentation result of the source domain image.

In another implementation, in step 301, the source domain samples include a first sample set and a second sample set. The computer device may train an initial image segmentation model by using the first sample set, to obtain the pre-trained image segmentation model, and then, retrain the pre-trained image segmentation model by using the second sample set. In this case, an input of the pre-trained image segmentation model is the second sample set in the source domain samples, and a predicted segmentation result of a source domain image in the second sample set is extracted.

The target domain image has been introduced in the embodiment in FIG. 1, and details are not described herein again. The target domain image is inputted to the pre-trained image segmentation model to extract the predicted segmentation result of the target domain image.

Step 303. Respectively input the predicted segmentation result of the source domain image and the predicted segmentation result of the target domain image to a first discriminator, to obtain a discrimination result of the first discriminator.

The first discriminator is used for discriminating whether the inputted segmentation result is from a source domain or a target domain, that is, the first discriminator performs a binary task. For example, a result of the first discriminator may be 0 or 1. When the result is 0, it indicates that the inputted segmentation result is from the source domain. When the result is 1, it indicates that the inputted segmentation result is from the target domain.

Step 304. Calculate a value of a discrimination loss function of the first discriminator according to the discrimination result of the first discriminator.

The discrimination loss function of the first discriminator is used for measuring a discrimination accuracy of the first discriminator.

The discrimination loss function $L_{D1}(P_T)$ of the first discriminator may be expressed as:

$$L_{D1}(P_T) = -\Sigma_{h,w}(1-z)\log(D(P_T)^{(h,w,0)}) + z\log(D(P_T)^{(h,w,1)}).$$

$z$ is a constant, when $z=1$, it indicates that an image is the target domain image, and when $z=0$, it indicates that the image is the source domain image.

$P_T$ is a predicted segmentation result of the target domain image, and may be expressed as:

$$P_T = G_{Seg}(X_T).$$

$G_{seg}$ represents an image segmentation model, $X_T$ represents the target domain image, and $P_T \in R^{H \times W \times C}$. H and W respectively represent a predicted segmentation height and width of the target domain image, and C represents a segmentation category.

Step 305. Adjust a parameter of the first discriminator by minimizing the value of the discrimination loss function of the first discriminator.

The value of the discrimination loss function reflects the discrimination accuracy of the first discriminator and is inversely proportional to the discrimination accuracy, that is, a smaller value of the discrimination loss function indicates a higher discrimination accuracy of the first discriminator. Therefore, during training, the computer device can adjust the parameter of the first discriminator by minimizing the value of the discrimination loss function, so that the first discriminator can discriminate as accurately as possible whether the inputted segmentation result is from the source domain or the target domain.

Step 306. Calculate a value of an adversarial loss function of the first discriminator according to the discrimination result of the first discriminator for the predicted segmentation result of the target domain image.

The adversarial loss function of the first discriminator is used for measuring a difference degree between the predicted segmentation result of the target domain image and the predicted segmentation result of the source domain image.

The adversarial loss function $L_{Adv1}(X_T)$ may be expressed as:

$$L_{Adv1}(X_T) = -\Sigma_{h,w} L_{MAE}(D(P_T)^{(h,w,1)}, z).$$

$X_T$ represents the target domain image, $L_{MAE}$ represents a mean absolute error loss function, and $z=0$ indicates that the segmentation result inputted to the discriminator is from the source domain.

Step 307. Respectively input the predicted segmentation result of the source domain image and the standard segmentation result of the source domain image to a second discriminator, to obtain a discrimination result of the second discriminator.

The second discriminator is used for discriminating whether the inputted segmentation result is the predicted segmentation result or the standard segmentation result. The second discriminator also performs a binary task. For example, a result of the second discriminator may be a number of 0 or 1. When the result is 0, it indicates that the inputted segmentation result is the predicted segmentation result of the source domain image. When the result is 1, it indicates that the inputted segmentation result is the standard segmentation result of the source domain image.

Step 308. Calculate a value of a discrimination loss function of the second discriminator according to the discrimination result of the second discriminator.

The discrimination loss function of the second discriminator is used for measuring a discrimination accuracy of the second discriminator.

The discrimination loss function $L_{D2}(P_S)$ of the second discriminator may be expressed as:

$$L_{D2}(P_S) = -\Sigma_{h,w}(1-u)\log(D(P_S)^{(h,w,0)}) + u\log(D(P_S)^{(h,w,1)}).$$

$P_S$ represents the predicted segmentation result of the source domain image, u is a constant, when $u=1$, it indicates that the image is the target domain image, and when $u=0$, it indicates that the image is the source domain image.

The predicted segmentation result $P_S$ of the source domain image may be expressed as:

$$P_S = G_{Seg}(X_S).$$

$G_{seg}$ represents the image segmentation model, and $X_S$ represents the source domain image.

Step 309. Adjust a parameter of the second discriminator by minimizing the value of the discrimination loss function of the second discriminator.

The value of the discrimination loss function reflects the discrimination accuracy of the second discriminator and is inversely proportional to the discrimination accuracy. Therefore, during training, the parameter of the second discriminator may be adjusted by minimizing the value of the discrimination loss function, so that the second discriminator can discriminate as accurately as possible whether the inputted segmentation result is the predicted segmentation result of the source domain image or the standard segmentation result of the source domain image.

Step 310. Calculate a value of an adversarial loss function of the second discriminator according to the discrimination result of the second discriminator for the predicted segmentation result of the source domain image.

The adversarial loss function of the second discriminator is used for measuring a difference degree between the predicted segmentation result of the source domain image and the standard segmentation result of the source domain image.

The adversarial loss function $L_{Adv2}(X_S)$ of the second discriminator may be expressed as:

$$L_{Adv2}(X_S) = -\Sigma_{h,w} L_{MAE}(D(P_S)^{(h,w,1)}, u).$$

$X_S$ represents the source domain image, $L_{MAE}$ represents a mean absolute error loss function, and $u=1$ indicates that the segmentation result inputted to the discriminator is the standard segmentation result of the source domain image.

Step 311. Construct a target function according to the loss function of the pre-trained image segmentation model, the adversarial loss function of the first discriminator, and the adversarial loss function of the second discriminator.

The loss function $L_{Seg}(X_S)$ of the pre-trained image segmentation model may use a cross entropy (CE) loss function, and an expression of the loss function is:

$$L_{Seg}(X_S) = -\Sigma_{h,w} \Sigma_{c \in C} Y_S^{(h,w,c)} \log(P_S^{(h,w,c)}).$$

$X_S$ represents the source domain image, and $Y_S$ represents the standard segmentation result of the source domain image.

The target function trained by the image segmentation model may be expressed as:

$$\max_{D} \min_{G_{Seg}} (\alpha_{Seg} L_{Seg}(X_S) + \alpha_{Adv1} L_{Adv1}(X_T) + \alpha_{Adv2} L_{Adv2}(X_S)).$$

$\alpha_{Seg}$, $\alpha_{Adv1}$, and $\alpha_{Adv2}$ are regulatory parameters used for balancing the loss function of the image segmentation model, the adversarial loss function of the first discriminator, and the adversarial loss function of the second discriminator.

$$\max_{D}$$

means to maximize values of the discrimination loss function of the first discriminator and the discrimination loss function of the second discriminator, and $$\min_{G_{Seg}}$$

means to minimize a value of the loss function of the image segmentation model and a value of a weighted sum of the adversarial loss function of the first discriminator and the adversarial loss function of the second discriminator.

Step 312. Adjust a parameter of the pre-trained image segmentation model by minimizing a value of the loss function of the image segmentation model and a value of a weighted sum of the adversarial loss function of the first discriminator and the adversarial loss function of the second discriminator and maximizing the values of the discrimination loss function of the first discriminator and the discrimination loss function of the second discriminator, to obtain a trained image segmentation model.

After the computer device obtains the value of the loss function of the image segmentation model and feeds back the values of the adversarial loss function of the first discriminator and the adversarial loss function of the second discriminator to an image segmentation network, the parameter of the image segmentation model is adjusted through the image segmentation network to: minimize the value of the loss function of the image segmentation model and the weighted sum of the adversarial loss function of the first discriminator and the adversarial loss function of the second discriminator; and maximize the values of the discrimination loss function of the first discriminator and the discrimination loss function of the second discriminator. Through adversarial training of a segmentation network and a discriminant network, the segmentation result of the source domain image and the segmentation result of the target domain image predicted by the image segmentation model are enabled to be as close as possible to the standard segmentation result of the source domain image.

Because the adversarial loss function of the first discriminator is minimized, the segmentation result of the source domain image gradually approaches the segmentation result of the target domain image. In this case, the segmentation result of the source domain image gradually moves away from the standard segmentation result of the source domain image, that is, the segmentation accuracy of the source domain image for the segmentation model is reduced. In this case, the adversarial loss function of the second discriminator is minimized, so that the segmentation result of the source domain image gradually approaches the standard segmentation result of the source domain image, and the segmentation result of the source domain image and the segmentation result of the target domain image predicted by the image segmentation model are as close as possible to the standard segmentation result of the source domain image.

When the image segmentation model satisfies a training stop condition, the computer device stops training the model and obtains the trained image segmentation model. The segmentation result of the target domain image for the trained image segmentation model is more similar to the standard segmentation result. The training stop condition of the image segmentation model may be set in advance. For example, a value of a loss function reaches a preset threshold, a number of training rounds reaches a preset number of rounds, or a training duration reaches a preset duration, which is not limited in this embodiment of this disclosure.

In some embodiments, before inputting the source domain image and the target domain image to the image segmentation model, the computer device performs normalization processing on the source domain image and the target domain image, to obtain a processed source domain image and a processed target domain image. For example, a pixel value of each pixel in the source domain image and the target domain image is normalized to be within the range [−1, 1]. The processed source domain image and the processed target domain image are used for training the image segmentation model.

In this embodiment of this disclosure, the first discriminator and the second discriminator share a parameter. In an example, the parameters of the first discriminator and the second discriminator are shared in real time. For example, in each round of training, when the parameter of the first discriminator is updated, the updated parameter is synchronized to the second discriminator. The second discriminator is trained with the synchronized parameter, re-updates the parameter, and synchronizes the re-updated parameter to the first discriminator. During training, the first discriminator and the second discriminator share the parameter in real time, helping improve a training efficiency of the model.

In some other examples, the first discriminator and the second discriminator only share the parameter during initial training, and then update the parameter independently. In this case, the second discriminator may be trained after the first discriminator, or the first discriminator may be trained after the second discriminator, or the first discriminator and the second discriminator may be trained simultaneously, which is not limited in this embodiment of this disclosure.

In some embodiments, initial learning rates of the image segmentation network, the first discriminator, and the second discriminator may be preset values. For example, the initial learning rates of the image segmentation network, the first discriminator, and the second discriminator are $1.5 \times 10^{-5}$, $1 \times 10^{-5}$, and $1 \times 10^{-5}$, respectively.

In summary, in the technical solution provided in this embodiment of this disclosure, the segmentation result of the source domain image and the segmentation result of the target domain image are inputted to the first discriminator, and the segmentation result of the source domain image and the standard segmentation result of the source domain image are inputted to the second discriminator, to obtain the discrimination loss function and the adversarial loss function of the first discriminator and the discrimination loss function and the adversarial loss function of the second discriminator. Subsequently, the loss function of the pre-trained image segmentation model, the adversarial loss function of the first discriminator, and the adversarial loss function of the second discriminator are fed back to the image segmentation model, and the parameter of the pre-trained image segmentation model is adjusted by minimizing the value of the loss function of the image segmentation model and the value of the weighted sum of the adversarial loss function of the first discriminator and the adversarial loss function of the second discriminator and maximizing the values of the discrimination loss function of the first discriminator and the discrimination loss function of the second discriminator, to obtain the trained image segmentation model. The trained image segmentation model can accurately segment an image from the target domain, and has good segmentation performance and generalization capabilities.

In some embodiments, before the source domain image and the target domain image are inputted to the image segmentation model, normalization processing is performed on the source domain image and the target domain image, so that an inputted image and a discrimination result of the discriminator are in the same dimension, to better train and optimize the image segmentation model.

Figure 4:
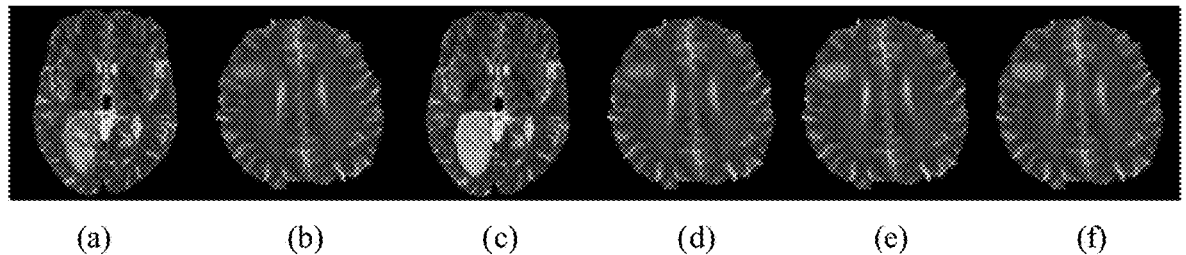
FIG. 4 is an exemplary schematic diagram of segmentation results in different segmentation manners.

FIG. 4 is an exemplary schematic diagram of segmentation results in different segmentation manners. (a) represents a source domain image; (b) represents a target domain image; (c) represents a segmentation result of the source domain image obtained by using an image segmentation model that is trained by only using the source domain image; (d) represents a segmentation result of a target domain image obtained by using an image segmentation model that is trained by using the source domain image and a standard segmentation result of the source domain image and that is trained without domain adaptive training; (e) represents a segmentation result of the target domain image obtained by using a trained image segmentation model obtained by using the training method provided in this solution; and (f) represents a standard segmentation result of the target domain image. It may be seen from FIG. 4 that the image segmentation model trained by using the method for training an image segmentation model provided in this solution can segment a target region and has good segmentation performance.

After the trained image segmentation model is obtained, the trained image segmentation model may be deployed in a computer device. When the computer device obtains a to-be-segmented image from a target domain, the trained image segmentation model is invoked, to accurately segment the target region from the image and obtain a segmentation result of the to-be-segmented image. Using an example in which the computer device is an auxiliary diagnosis platform in a hospital, the trained image segmentation model is deployed in the auxiliary diagnosis platform. The auxiliary diagnosis platform can directly segment accurate distribution information of a lesion region when acquiring a medical image of a patient, for a doctor to make an accurate diagnosis.

Beneficial effects of this solution are further described below by testing this solution on three different image datasets.

The three datasets are a brain tumor segmentation (BRATS) 2018 dataset, a glioma private dataset, and a multi-center spinal cord gray matter (SCGM) segmentation 2017 dataset respectively.

The BRATS 2018 dataset includes 285 samples with label sets, and each sample includes four modalities, namely, fluid-attenuated inversion recovery (FLAIR), T1 enhancement, T1 MRI, and T2 MRI. Preprocessing of the foregoing data includes skull peeling, registration, and resampling to a resolution of 1×1×1 mm$^3$, and a dimension of each sample is 240×240×155. During a test, only a T2 MRI dataset in the dataset is used, and a 3D T2 MRI axonometric image is converted into a multi-layer 2D image.

The glioma private dataset includes 200 samples with label sets, each sample has only a dataset of slice thickness 3D T2 MM, and the label set only marks a tumor edema region (that is, an entire tumor region). Because the dataset is obtained by thick layer scanning, that is, only a structure of the axial image is clear, and images of other two views (that is, a coronal diagram and a sagittal diagram) are very blurry. Therefore, during the test, only an axial plane is used, and the 3D T2 MRI axonometric image is converted into the multi-layer 2D image. The 2D image is resampled to a size of 513×513. In addition, the foregoing data preprocessing is only skull peeling.

The SCGM 2017 dataset includes data from four different centers, including a total of 40 samples with label sets. Dimensions of the data are from 0.25×0.25×0.25 mm$^3$ to 0.5×0.5×0.5 mm$^3$, and the 3D T2 MRI axonometric image is converted into the multi-layer 2D image.

In a brain tumor segmentation task, two test solutions are designed: Test 1. Use BRATS 2018 data as source domain data, and glioma private data as target domain data. Test 2. Use glioma private data as source domain data, and BRATS 2018 data as target domain data. In addition, on the basis of using a DeepLabv3+ model as a segmentation model, a DeepLabv2 model is further used as a segmentation model for comparison. Moreover, in this solution, an adversarial discriminative domain adaptation (ADDA) segmentation algorithm performed in an output space is compared with the ADDA segmentation algorithm performed in a feature space.

Table-1 shows test results of test 1 and test 2 in the brain tumor segmentation task.

TABLE 1

|  | Dice score | | Sensitivity | | Specificity | | Hausdorff distance | |
| --- | --- | --- | --- | --- | --- | --- | --- | --- |
|  | P | B | P | B | P | B | P | B |
| DeepLabv2 | 0.54 | 0.60 | 0.64 | 0.53 | 0.92 | 0.88 | 30.25 | 25.43 |
| DeepLabv3+ | 0.61 | 0.61 | 0.70 | 0.55 | 0.96 | 0.90 | 38.22 | 25.01 |
| ADDA | 0.62 | 0.62 | 0.68 | 0.56 | 0.92 | 0.91 | 27.13 | 24.16 |
| $^1$Ours | 0.60 | 0.65 | 0.71 | 0.59 | 0.96 | 0.92 | 31.35 | 23.55 |
| $^2$Ours | 0.63 | 0.67 | 0.70 | 0.62 | 0.91 | 0.97 | 24.29 | 23.77 |

The first row is measurement indicators of image segmentation. Dice score is used for measuring a similarity between two sets. Sensitivity represents a proportion of accurate segmentation results among all test results. Specificity measures how well a test can identify true negatives. Hausdorff distance is a distance defined between any two sets in a metric space. The Dice score, Sensitivity, and Specificity are in direct proportion to accuracy of an image segmentation model, and Hausdorff distance is inversely proportional to the accuracy of the image segmentation model. P in the second row indicates that the glioma private data is used as the source domain data, the BRATS 2018 data is used as the target domain data. B in the second row indicates that the BRATS 2018 data is used as the source domain data, and the glioma private data is used as the target domain data. The third row to the fifth row respectively represent the test results obtained by using the DeepLabv3+ segmentation model, the DeepLabv2 segmentation model, and the ADDA segmentation algorithm. $^1$Ours in the sixth row represents the test results obtained by using the DeepLabv2 model as the segmentation model in this solution. $^2$Ours in the seventh row represents the test results obtained by using the DeepLabv3+ model as the segmentation model in this solution. It may be seen from Table-1 that the test results in this solution are more accurate than that of the foregoing three related segmentation models and segmentation algorithms. In addition, comparing the test results in the sixth row and the seventh row, it may be seen that better segmentation results can be obtained by using the DeepLabv3+ model as the segmentation model in this solution.

Figure 5:
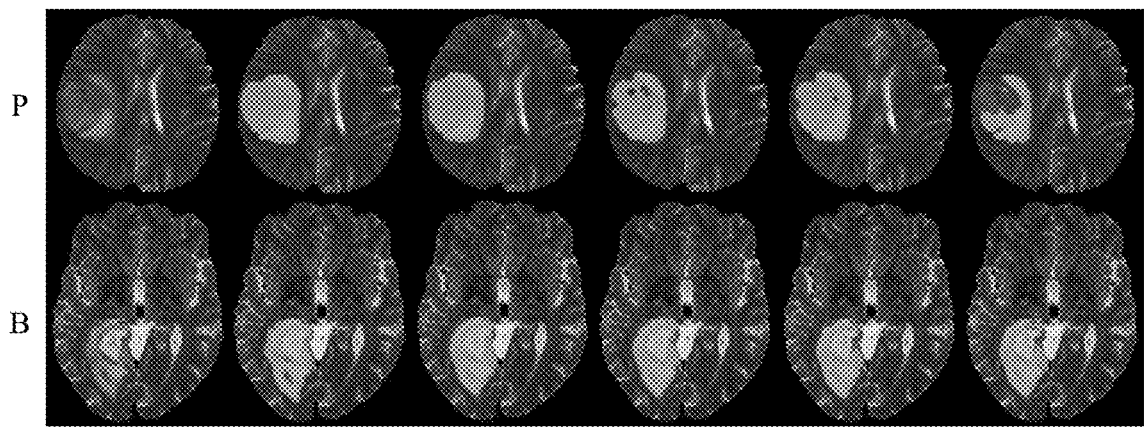
FIG. 5 is a sample graph of segmentation results of a brain tumor in different segmentation manners.

FIG. 5 is a sample graph of segmentation results of a brain tumor in different segmentation manners. A row P represents test results obtained by using glioma private data as source domain data and BRATS 2018 data as target domain data. A row B represents the test results obtained by using the BRATS 2018 data as the source domain data and the glioma private data as the target domain data. A first column Axial represents a data axial graph. A second column represents a ground truth (GT, segmentation standard) graph. A third column represents test results obtained after a DeepLabv3+ model is used as a segmentation model and domain adaptation (DA) is performed, that is, the test results in this solution. A fourth column represents test results obtained after the DeepLabv3+ model is only used as the segmentation model and the DA is not performed. A fifth column represents test results obtained after a DeepLabv2 model is used as the segmentation model and the DA is performed. A sixth column represents test results obtained by using only the DeepLabv3+ model as the segmentation model and the DA is not performed. It may be intuitively seen from FIG. 5 that in the technical solution of this application, a target domain image can be accurately segmented.

In an SCGM segmentation task, referring to the related technical solutions, two test solutions are designed: Test 1. Use data of a center 1 and a center 2 as source domain data, and use data of a center 3 as target domain data. Test 2. Use data of a center 1 and a center 2 as source domain data, and use data of a center 4 as target domain data. Results of the two test solutions are compared with segmentation results of the two related technical solutions in which an exponential moving average (EMA) segmentation model and an unsupervised domain adaptation with self-ensembling (UDASE) segmentation model are used. The two test solutions designed in this application are the same as the test solutions provided in related technologies, so as to compare effects of the technical solutions provided in this application with effects of the technical solutions provided in the related technologies.

Table-2 shows test results of test 1 and test 2 in the SCGM segmentation task.

TABLE 2

| Adaptation | Methods | Dice score | Sensitivity | Specificity | Hausdorff distance |
|---|---|---|---|---|---|
| Center 3 | DeepLabv3+ | 0.75 | 0.90 | 0.98 | 5.40 |
| | EMA | 0.83 | 0.91 | 0.99 | 2.13 |
| | UDASE | 0.85 | 0.87 | 0.99 | 2.02 |
| | Ours | 0.80 | 0.83 | 0.99 | 4.04 |
| Center 4 | DeepLabv3+ | 0.81 | 0.79 | 0.99 | 2.90 |
| | EMA | 0.69 | 0.97 | 0.99 | 2.48 |
| | UDASE | 0.75 | 0.95 | 0.99 | 2.36 |
| | Ours | 0.83 | 0.83 | 0.99 | 2.01 |

The row where DeepLabv3+ is located represents test results obtained by using a DeepLabv3+ model as a segmentation model. The rows where EMA and the UDASE are located represent test results of the related technologies. The row where Ours is located represents test results of this solution. It may be seen from Table-2 that for test 2, that is, in a test in which the data of the center 1 and center 2 as the source domain data is adapted to the center 4, segmentation performance of the segmentation model of this solution is significantly better than that of the solution provided in the related technologies. For test 1, that is, in a test in which the data of the center 1 and center 2 as the source domain data is adapted to the center 3, by comparing the test result of the segmentation model of this solution with that of segmentation by only using the DeepLabv3+ model without adaption, this solution can significantly improve the segmentation performance of the target domain data.

Figure 6:
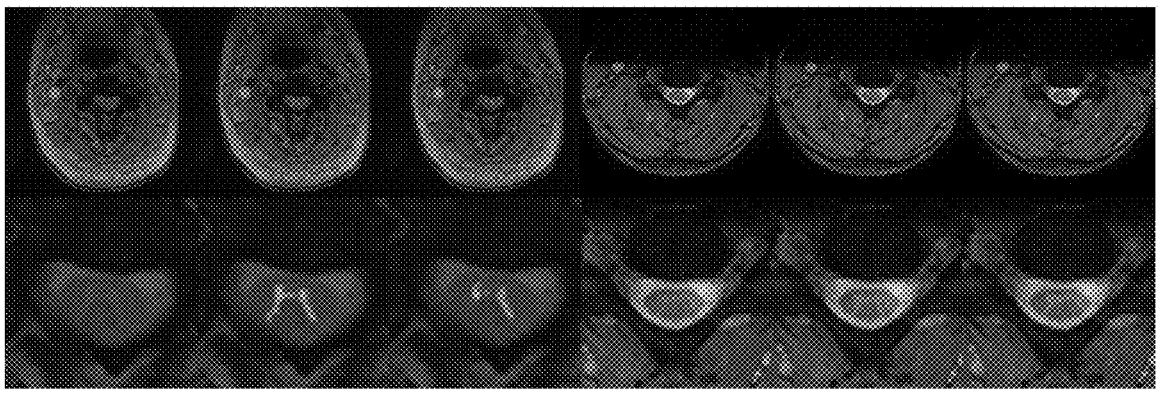
FIG. 6 is a sample graph of segmentation results of spinal cord gray matter (SCGM) in different segmentation manners.

FIG. 6 is a sample graph of segmentation results of SCGM in different segmentation manners. A first column and a fourth column respectively represent segmentation results obtained by using related technologies in test 1 and test 2. A second column and a fifth column respectively represent test results obtained in test 1 and test 2 after the DeepLabv3+ model is used as the segmentation model and DA is performed, that is, the test results of this solution. A third column and a sixth column respectively represent test results obtained in test 1 and test 2 by using only the DeepLabv3+ model as the segmentation model and the DA is not performed. It may be intuitively seen from FIG. 6 that in the technical solution of this application, a target domain image can be accurately segmented, and image visual information outputted by the target domain image in an output space is clearer and more accurate.

In conclusion, in the technical solution of this application, after the DeepLabv3+ model is used as the segmentation model and the DA is performed in the output space, the segmentation performance and generalization capabilities of a final trained image segmentation model are improved, so that the image segmentation model can accurately segment the target domain image, and a segmentation result of the target domain image is more accurate.

It is to be understood that, although each step of the flowcharts in FIG. 1 and FIG. 3 is displayed sequentially according to arrows, the steps are not necessarily performed according to an order indicated by arrows. Unless clearly specified in this specification, there is no strict sequence limitation on the execution of the steps, and the steps may be performed in another sequence. Moreover, at least some of the steps in FIG. 1 and FIG. 3 may include a plurality of sub-steps or a plurality of stages. The sub-steps or stages are not necessarily performed at the same moment, but may be performed at different moments. The sub-steps or stages are not necessarily performed sequentially, but may be performed with at least one part of the other steps or sub-steps of other steps or stages in turn.

The following describes apparatus embodiments of this disclosure, which can be used for executing the method embodiments of this disclosure. For details not disclosed in the apparatus embodiments of this disclosure, refer to the method embodiments of this disclosure.

In this disclosure, the term module (and other similar terms such as unit, submodule, etc.) i may refer to a software module, a hardware module, or a combination thereof. A software module (e.g., computer program) may be developed using a computer programming language. A hardware module may be implemented using processing circuitry and/or memory. Each module can be implemented using one or more processors (or processors and memory). Likewise, a processor (or processors and memory) can be used to implement one or more modules. Moreover, each module can be part of an overall module that includes the functionalities of the module.

Figure 7:
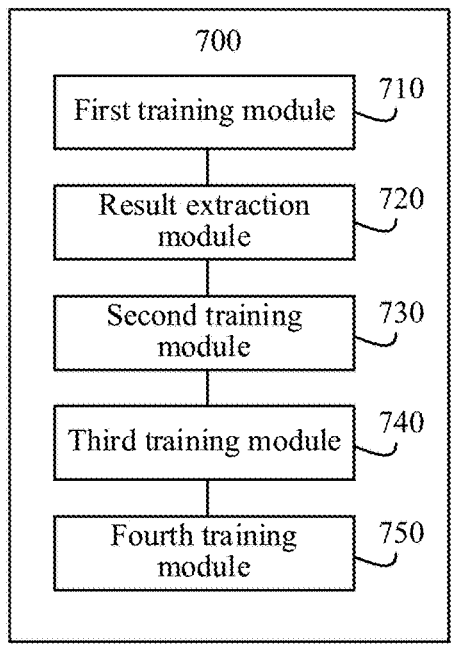
FIG. 7 is a block diagram of an apparatus for training an image segmentation model according to an embodiment of this disclosure.

FIG. 7 is a block diagram of an apparatus for training an image segmentation model according to an embodiment of this disclosure. The apparatus has functions of implementing examples of the method for training an image segmentation model. The functions may be implemented by using hardware, or may be implemented by hardware executing corresponding software. The apparatus may be the computer device described above, or may be disposed on the computer device. The apparatus 700 may include: a first training module 710, a result extraction module 720, a second training module 730, a third training module 740, and a fourth training module 750.

The first training module 710 is configured to train an initial image segmentation model by using source domain samples, to obtain a pre-trained image segmentation model, the source domain samples including a source domain image and a standard segmentation result of the source domain image.

The result extraction module 720 is configured to extract a predicted segmentation result of the source domain image and a predicted segmentation result of a target domain image by using the pre-trained image segmentation model.

The second training module 730 is configured to train a first discriminator by using the predicted segmentation result of the source domain image and the predicted segmentation result of the target domain image, the first discriminator being used for discriminating whether an inputted segmentation result is from a source domain or a target domain.

The third training module 740 is configured to train a second discriminator by using the predicted segmentation result of the source domain image and the standard segmentation result of the source domain image, the second discriminator being used for discriminating whether an inputted segmentation result is the predicted segmentation result or the standard segmentation result.

The fourth training module 750 is configured to retrain the pre-trained image segmentation model according to a loss function of the pre-trained image segmentation model, an adversarial loss function of the first discriminator, and an adversarial loss function of the second discriminator, such iterative loop training being performed until converging to obtain a trained image segmentation model.

In summary, in the technical solution provided in this embodiment of this disclosure, predicted segmentation results of a source domain image and a target domain image are extracted by using an image segmentation model pre-trained by using source domain samples. Further, the predicted segmentation results of the source domain image and the target domain image are inputted to a first discriminator, and the predicted segmentation result of the source domain image and a standard segmentation result of the source domain image are inputted to a second discriminator. The pre-trained image segmentation model is retrained by using an adversarial learning idea, and such iterative loop training is performed until the model converges, to obtain a trained image segmentation model. In the technical solutions provided in this application, the source domain image and the target domain image are aligned in the output space, so that the trained image segmentation model can reduce, in the output space, a difference between the source domain image and the target domain image, and reduce an error in segmentation of a target domain by of the trained image segmentation model, to enable a segmentation result of the target domain image to be more accurate.

In some embodiments, the second training module 730 is configured to respectively input the predicted segmentation result of the source domain image and the predicted segmentation result of the target domain image to the first discriminator, to obtain a discrimination result of the first discriminator; calculate a value of a discrimination loss function of the first discriminator according to the discrimination result of the first discriminator, the discrimination loss function of the first discriminator being used for measuring a discrimination accuracy of the first discriminator; and adjust a parameter of the first discriminator by minimizing the value of the discrimination loss function of the first discriminator.

Figure 8:
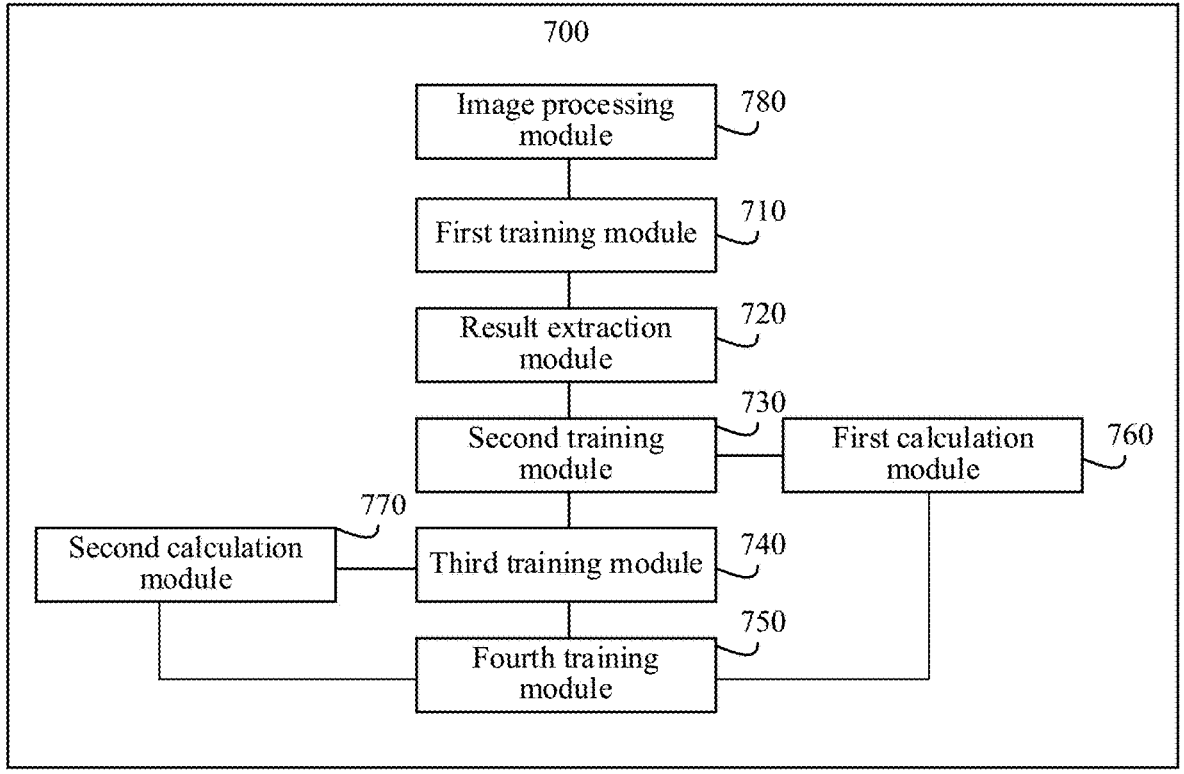
FIG. 8 is a block diagram of an apparatus for training an image segmentation model according to an embodiment of this disclosure.

In some embodiments, referring to FIG. 8, the apparatus 700 further includes a first calculation module 760.

The first calculation module 760 is configured to calculate a value of the adversarial loss function of the first discriminator according to the discrimination result of the first discriminator for the predicted segmentation result of the target domain image, the adversarial loss function of the first discriminator being used for measuring a difference degree between the predicted segmentation result of the target domain image and the predicted segmentation result of the source domain image.

In some embodiments, the third training module 740 is configured to respectively input the predicted segmentation result of the source domain image and the standard segmentation result of the source domain image to the second discriminator, to obtain a discrimination result of the second discriminator; calculate a value of a discrimination loss function of the second discriminator according to the discrimination result of the second discriminator, the discrimination loss function of the second discriminator being used for measuring a discrimination accuracy of the second discriminator; and adjust a parameter of the second discriminator by minimizing the value of the discrimination loss function of the second discriminator.

In some embodiments, referring to FIG. 8, the apparatus 700 further includes a second calculation module 770.

The second calculation module 770 is configured to calculate a value of an adversarial loss function of the second discriminator according to the discrimination result of the second discriminator for the predicted segmentation result of the source domain image, the adversarial loss function of the second discriminator being used for measuring a difference degree between the predicted segmentation result of the source domain image and the standard segmentation result of the source domain image.

In some embodiments, the fourth training module 750 is configured to construct a target function according to the loss function of the pre-trained image segmentation model, the adversarial loss function of the first discriminator, and the adversarial loss function of the second discriminator; and adjust a parameter of the image segmentation model by minimizing a value of the loss function of the pre-trained image segmentation model and a value of a weighted sum of the adversarial loss function of the first discriminator and the adversarial loss function of the second discriminator and maximizing the value of the discrimination loss function of the first discriminator and the value of the discrimination loss function of the second discriminator, to obtain the trained image segmentation model.

In some embodiments, the first discriminator and the second discriminator share a parameter.

In some embodiments, referring to FIG. 8, the apparatus 700 further includes an image processing module 780.

The image processing module 780 is configured to perform normalization processing on the source domain image and the target domain image, to obtain a processed source domain image and a processed target domain image, the processed source domain image and the processed target domain image being used for training the image segmentation model.

In some embodiments, an image segmentation apparatus may be provided. The apparatus has functions of implementing examples of the image segmentation method. The functions may be implemented by using hardware, or may be implemented by hardware executing corresponding software. The apparatus may be the computer device described above, or may be disposed on the computer device. The apparatus may include: an obtaining module and an invoking module.

The obtaining module is configured to obtain a to-be-segmented image from a target domain.

The invoking module is configured to process the to-be-segmented image by invoking a trained image segmentation model, to obtain a segmentation result of the to-be-segmented image, the trained image segmentation model being obtained by training an image segmentation model through adversarial learning in an output space by using a first discriminator and a second discriminator.

The first discriminator is used for reducing a difference between a predicted segmentation result of a target domain image and a predicted segmentation result of a source domain image in a process of training the image segmentation model, and the second discriminator is used for reducing a difference between the predicted segmentation result of the source domain image and a standard segmentation result of the source domain image in the process of training the image segmentation model.

When the apparatus provided in the foregoing embodiments implements functions of the apparatus, the division of the foregoing functional modules is merely an example for description. In the practical application, the functions may be assigned to and completed by different functional modules according to the requirements, that is, the internal structure of the device is divided into different functional modules, to implement all or some of the functions described above. In addition, the apparatus provided in the foregoing embodiment belongs to the same conception as the embodiment of the method. For a specific implementation process thereof, reference may be made to the method embodiment. Details are not described herein again.

Figure 9:
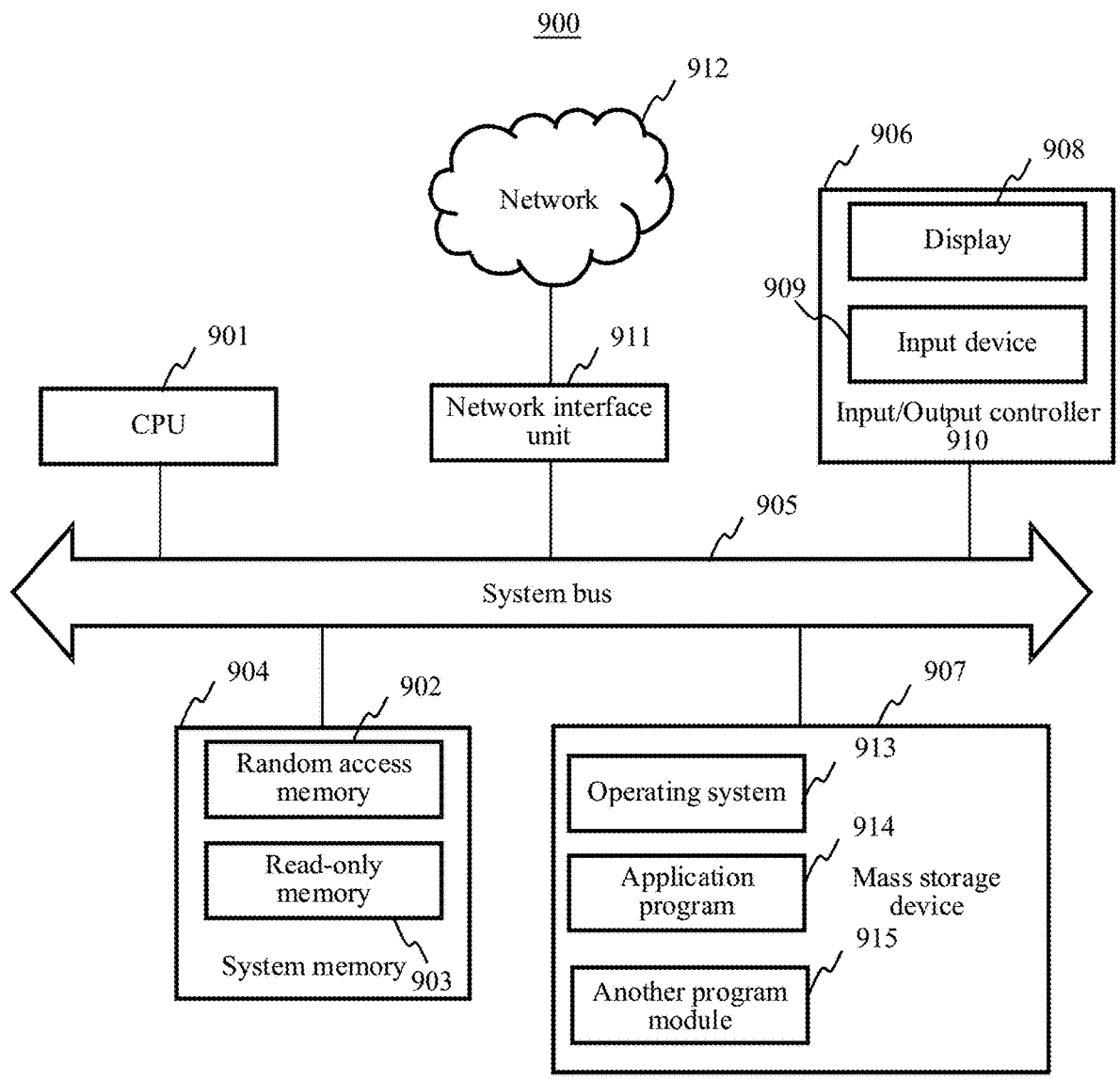
FIG. 9 is a schematic structural diagram of a computer device according to an embodiment of this disclosure.

FIG. 9 is a schematic structural diagram of a computer device according to an embodiment of this disclosure. The computer device may be any electronic device with a data processing function and a data storage function, for example, a PC or a server. The computer device is configured to perform the method for training an image segmentation model provided in the foregoing embodiments. Specifically:

The computer device 900 includes a central processing unit (CPU) 901, a system memory 904 including a random access memory (RAM) 902 and a read-only memory (ROM) 903, and a system bus 905 connecting the system memory 904 and the CPU 901. The computer device 900 further includes a basic input/output (I/O) system 906 configured to transmit information between components in a computer, and a mass storage device 907 configured to store an operating system 913, an application program 914, and another program module 912.

The basic I/O system 906 includes a display 908 configured to display information, and an input device 909 used by a user to input information, such as a mouse or a keyboard. The display 908 and the input device 909 are both connected to the central processing unit 901 through an input/output controller 910 connected to the system bus 905. The basic I/O system 906 may further include the I/O controller 910 for receiving and processing input from a plurality of other devices such as a keyboard, a mouse, an electronic stylus, or the like. Similarly, the input/output controller 910 further provides an output to a display screen, a printer, or other types of output devices.

The mass storage device 907 is connected to the CPU 901 through a mass storage controller (not shown) connected to the system bus 905. The mass storage device 907 and an associated computer-readable medium provide non-volatile storage for the computer device 900. In other words, the mass storage device 907 may include a non-transitory computer-readable medium (not shown) such as a hard disk or a CD-ROM drive.

Without loss of generality, the non-transitory computer-readable medium may include a computer storage medium and a communication medium. The non-transitory computer-storage medium includes volatile and non-volatile media, and removable and non-removable media implemented by using any method or technology used for storing information such as computer-readable instructions, data structures, program modules, or other data. The non-transitory computer-readable storage medium may include a ROM, a programmable ROM (PROM), an electrically programmable ROM (EPROM), an electrically erasable programmable ROM (EEPROM) or a flash memory. The volatile memory may include a RAM or an external high-speed cache. For the purpose of description instead of limitation, the RAM is available in a plurality of forms, such as a static RAM (SRAM), a dynamic RAM (DRAM), a synchronous DRAM (SDRAM), a double data rate SDRAM (DDRSDRAM), an enhanced SDRAM (ESDRAM), a synchronous link (Synchlink) DRAM (SLDRAM), a RAM bus (Rambus) direct RAM (RDRAM), a direct Rambus dynamic RAM (DRDRAM), and a Rambus dynamic RAM (RDRAM). Certainly, a person skilled in the art may learn that the non-transitory computer storage medium is not limited to the foregoing several types. The system memory 904 and the mass storage device 907 may be collectively referred to as a memory.

According to the various embodiments of this disclosure, the computer device 900 may further be connected, through a network such as the Internet, to a remote computer on the network for running. That is, the computer device 900 may be connected to a network 912 by using a network interface unit 911 connected to the system bus 905, or may be connected to another type of network or a remote computer system (not shown) by using a network interface unit 911.

The memory further includes at least one instruction, at least one program, a code set, or an instruction set. The at least one instruction, the at least one program, the code set, or the instruction set is stored in the memory and is configured to be executed by one or more processors to implement the method for training an image segmentation model or the image segmentation method.

In an exemplary embodiment, a computer device is further provided. The computer device may include a terminal. The computer device includes a processor and a memory, the memory storing at least one instruction, at least one program, a code set or an instruction set, the at least one instruction, the at least one program, the code set or the instruction set being loaded and executed by the processor to implement the method for training an image segmentation model or the image segmentation method.

In an exemplary embodiment, a non-transitory computer-readable storage medium is further provided, the non-transitory storage medium storing at least one instruction, at least one program, a code set, or an instruction set, and the at least one instruction, the at least one program, the code set, or the instruction set, when executed by a processor, implementing the method for training an image segmentation model or the image segmentation method.

In an exemplary embodiment, a computer program product is further provided, the computer program product, when executed by a processor, being configured to perform the method for training an image segmentation model or the image segmentation method provided in the foregoing embodiments.

"A plurality of" mentioned in the specification means two or more. "And/or" describes an association relationship between associated objects and represents that three relationships may exist. For example, A and/or B may represent the following three cases: only A exists, both A and B exist, and only B exists. The character "/" generally indicates an "or" relationship between the associated objects.

The technical features in the foregoing embodiments may be randomly combined. For concise description, not all possible combinations of the technical features in the embodiments are described. However, combinations of the technical features shall all be considered as falling within the scope described in this specification provided that the combinations of the technical features do not conflict with each other. The foregoing embodiments only describe several implementations of this application specifically and in detail, but cannot be construed as a limitation to the patent scope of this application. For a person of ordinary skill in the art, several transformations and improvements can be made without departing from the idea of this application, which all fall within the protection scope of this application. Therefore, the protection scope of this application shall be subject to the protection scope of the appended claims.

What is claimed is:

1. A method for training an image segmentation model, performed by a computer device, the method comprising:
    training an initial image segmentation model by using source domain samples, to obtain a pre-trained image segmentation model, the source domain samples comprising a source domain image and a standard segmentation result of the source domain image;
    extracting a predicted segmentation result of the source domain image and a predicted segmentation result of a target domain image by using the pre-trained image segmentation model;
    training a first discriminator by using the predicted segmentation result of the source domain image and the predicted segmentation result of the target domain image, the first discriminator being used for discriminating whether an inputted segmentation result is from a source domain or a target domain;
    training a second discriminator by using the predicted segmentation result of the source domain image and the standard segmentation result of the source domain image, the second discriminator being used for discriminating whether the inputted segmentation result is the predicted segmentation result or the standard segmentation result; and
    iteratively training the pre-trained image segmentation model according to a loss function of the pre-trained image segmentation model, a first adversarial loss function of the first discriminator, and a second adversarial loss function of the second discriminator, until convergence, to obtain a trained image segmentation model.

2. The method according to claim 1, wherein training the first discriminator by using the predicted segmentation result of the source domain image and the predicted segmentation result of the target domain image comprises:
    respectively inputting the predicted segmentation result of the source domain image and the predicted segmentation result of the target domain image to the first discriminator, to obtain a first discrimination result of the first discriminator for the predicted segmentation result of the source domain image and a second discrimination result of the first discriminator for the predicted segmentation result of the target domain image;
    calculating a value of a discrimination loss function of the first discriminator according to the first discrimination result and the second discrimination result, the discrimination loss function of the first discriminator being used for measuring a discrimination accuracy of the first discriminator; and
    adjusting a parameter of the first discriminator by minimizing the value of the discrimination loss function of the first discriminator.

3. The method according to claim 2, wherein after respectively inputting the predicted segmentation result of the source domain image and the predicted segmentation result of the target domain image to the first discriminator, to obtain the first discrimination result and the second discrimination result, the method further comprises:
    calculating a value of the first adversarial loss function of the first discriminator according to the second discrimination result, the first adversarial loss function of the first discriminator being used for measuring a difference degree between the predicted segmentation result of the target domain image and the predicted segmentation result of the source domain image.

4. The method according to claim 1, wherein training the second discriminator by using the predicted segmentation result of the source domain image and the standard segmentation result of the source domain image comprises:
    respectively inputting the predicted segmentation result of the source domain image and the standard segmentation result of the source domain image to the second discriminator, to obtain a third discrimination result of the second discriminator for the predicted segmentation result of the source domain image and a fourth discrimination result of the second discriminator for the standard segmentation result of the source domain image;
    calculating a value of a discrimination loss function of the second discriminator according to the third discrimination result and the fourth discrimination result, the discrimination loss function of the second discriminator being used for measuring a discrimination accuracy of the second discriminator; and
    adjusting a parameter of the second discriminator by minimizing the value of the discrimination loss function of the second discriminator.

5. The method according to claim 4, wherein after respectively inputting the predicted segmentation result of the source domain image and the standard segmentation result of the source domain image to the second discriminator, to obtain the third discrimination result and the fourth discrimination result, the method further comprises:
    calculating a value of the second adversarial loss function of the second discriminator according to the third discrimination result, the second adversarial loss function of the second discriminator being used for measuring a difference degree between the predicted segmentation result of the source domain image and the standard segmentation result of the source domain image.

6. The method according to claim 1, wherein iteratively training the pre-trained image segmentation model according to the loss function of the pre-trained image segmentation model, the first adversarial loss function of the first discriminator, and the second adversarial loss function of the second discriminator, until convergence, to obtain a trained image segmentation model comprises iteratively performing until convergence:
    constructing a target function according to the loss function of the pre-trained image segmentation model, the first adversarial loss function of the first discriminator, and the second adversarial loss function of the second discriminator; and
    adjusting a parameter of the pre-trained image segmentation model by minimizing a value of the loss function of the pre-trained image segmentation model and a value of a weighted sum of the first adversarial loss function of the first discriminator and the second adversarial loss function of the second discriminator and maximizing a value of a discrimination loss function of the first discriminator and a value of a discrimination loss function of the second discriminator, to obtain the trained image segmentation model.

7. The method according to claim 1, wherein the first discriminator and the second discriminator share a parameter.

8. The method according to claim 1, further comprising:
performing normalization processing on the source domain image and the target domain image, to obtain a processed source domain image and a processed target domain image, the processed source domain image and the processed target domain image being used for training the image segmentation model.

9. A device for training an image segmentation model, comprising a memory for storing instructions and a processor in communication with the memory, wherein the processor is configured to execute the instructions to cause the device to:
train an initial image segmentation model by using source domain samples, to obtain a pre-trained image segmentation model, the source domain samples comprising a source domain image and a standard segmentation result of the source domain image;
extract a predicted segmentation result of the source domain image and a predicted segmentation result of a target domain image by using the pre-trained image segmentation model;
train a first discriminator by using the predicted segmentation result of the source domain image and the predicted segmentation result of the target domain image, the first discriminator being used for discriminating whether an inputted segmentation result is from a source domain or a target domain;
train a second discriminator by using the predicted segmentation result of the source domain image and the standard segmentation result of the source domain image, the second discriminator being used for discriminating whether the inputted segmentation result is the predicted segmentation result or the standard segmentation result; and
iteratively train the pre-trained image segmentation model according to a loss function of the pre-trained image segmentation model, a first adversarial loss function of the first discriminator, and a second adversarial loss function of the second discriminator, until convergence, to obtain a trained image segmentation model.

10. The device according to claim 9, wherein, when the processor is configured to cause the device to train the first discriminator by using the predicted segmentation result of the source domain image and the predicted segmentation result of the target domain image, the processor is configured to cause the device to:
respectively input the predicted segmentation result of the source domain image and the predicted segmentation result of the target domain image to the first discriminator, to obtain a first discrimination result of the first discriminator for the predicted segmentation result of the source domain image and a second discrimination result of the first discriminator for the predicted segmentation result of the target domain image;
calculate a value of a discrimination loss function of the first discriminator according to the first discrimination result and the second discrimination result, the discrimination loss function of the first discriminator being used for measuring a discrimination accuracy of the first discriminator; and
adjust a parameter of the first discriminator by minimizing the value of the discrimination loss function of the first discriminator.

11. The device according to claim 10, wherein, after the processor is configured to cause the device to respectively input the predicted segmentation result of the source domain image and the predicted segmentation result of the target domain image to the first discriminator, to obtain the first discrimination result and the second discrimination result, the processor is configured to further cause the device to:
calculate a value of the first adversarial loss function of the first discriminator according to the second discrimination result, the first adversarial loss function of the first discriminator being used for measuring a difference degree between the predicted segmentation result of the target domain image and the predicted segmentation result of the source domain image.

12. The device according to claim 9, wherein, when the processor is configured to cause the device to train the second discriminator by using the predicted segmentation result of the source domain image and the standard segmentation result of the source domain image, the processor is configured to cause the device to:
respectively input the predicted segmentation result of the source domain image and the standard segmentation result of the source domain image to the second discriminator, to obtain a third discrimination result of the second discriminator for the predicted segmentation result of the source domain image and a fourth discrimination result of the second discriminator for the standard segmentation result of the source domain image;
calculate a value of a discrimination loss function of the second discriminator according to the third discrimination result and the fourth discrimination result, the discrimination loss function of the second discriminator being used for measuring a discrimination accuracy of the second discriminator; and
adjust a parameter of the second discriminator by minimizing the value of the discrimination loss function of the second discriminator.

13. The device according to claim 12, wherein, after the processor is configured to cause the device to respectively input the predicted segmentation result of the source domain image and the standard segmentation result of the source domain image to the second discriminator, to obtain the third discrimination result and the fourth discrimination result, the processor is configured to further cause the device to:
calculate a value of the second adversarial loss function of the second discriminator according to the third discrimination result, the second adversarial loss function of the second discriminator being used for measuring a difference degree between the predicted segmentation result of the source domain image and the standard segmentation result of the source domain image.

14. The device according to claim 9, wherein, when the processor is configured to cause the device to iteratively train the pre-trained image segmentation model according to the loss function of the pre-trained image segmentation model, the first adversarial loss function of the first discriminator, and the second adversarial loss function of the second discriminator, until convergence, to obtain a trained image segmentation model, the processor is configured to cause the device to iteratively perform until convergence:

constructing a target function according to the loss function of the pre-trained image segmentation model, the first adversarial loss function of the first discriminator, and the second adversarial loss function of the second discriminator; and adjusting a parameter of the pre-trained image segmentation model by minimizing a value of the loss function of the pre-trained image segmentation model and a value of a weighted sum of the first adversarial loss function of the first discriminator and the second adversarial loss function of the second discriminator and maximizing a value of a discrimination loss function of the first discriminator and a value of a discrimination loss function of the second discriminator, to obtain the trained image segmentation model.

15. The device according claim 9, wherein the first discriminator and the second discriminator share a parameter.

16. The device according to claim 9, wherein, when the processor executes the instructions, the processor is configured to further cause the device to:

perform normalization processing on the source domain image and the target domain image, to obtain a processed source domain image and a processed target domain image, the processed source domain image and the processed target domain image being used for training the image segmentation model.

17. A non-transitory storage medium for storing computer readable instructions, the computer readable instructions, when executed by a processor to predict an attribute of a target object based on machine learning, causing the processor to:

train an initial image segmentation model by using source domain samples, to obtain a pre-trained image segmentation model, the source domain samples comprising a source domain image and a standard segmentation result of the source domain image;

extract a predicted segmentation result of the source domain image and a predicted segmentation result of a target domain image by using the pre-trained image segmentation model;

train a first discriminator by using the predicted segmentation result of the source domain image and the predicted segmentation result of the target domain image, the first discriminator being used for discriminating whether an inputted segmentation result is from a source domain or a target domain;

train a second discriminator by using the predicted segmentation result of the source domain image and the standard segmentation result of the source domain image, the second discriminator being used for discriminating whether the inputted segmentation result is the predicted segmentation result or the standard segmentation result; and iteratively train the pre-trained image segmentation model according to a loss function of the pre-trained image segmentation model, a first adversarial loss function of the first discriminator, and a second adversarial loss function of the second discriminator, until convergence, to obtain a trained image segmentation model.

18. The non-transitory storage medium according to claim 17, wherein, when the computer readable instructions cause the processor to train the first discriminator by using the predicted segmentation result of the source domain image and the predicted segmentation result of the target domain image, the computer readable instructions cause the processor to:

respectively input the predicted segmentation result of the source domain image and the predicted segmentation result of the target domain image to the first discriminator, to obtain a first discrimination result of the first discriminator for the predicted segmentation result of the source domain image and a second discrimination result of the first discriminator for the predicted segmentation result of the target domain image;

calculate a value of a discrimination loss function of the first discriminator according to the first discrimination result and the second discrimination result, the discrimination loss function of the first discriminator being used for measuring a discrimination accuracy of the first discriminator; and adjust a parameter of the first discriminator by minimizing the value of the discrimination loss function of the first discriminator.

19. The non-transitory storage medium according to claim 18, wherein, after the computer readable instructions cause the processor to respectively input the predicted segmentation result of the source domain image and the predicted segmentation result of the target domain image to the first discriminator, to obtain the first discrimination result and the second discrimination result, the computer readable instructions further cause the processor to:

calculate a value of the first adversarial loss function of the first discriminator according to the second discrimination result, the first adversarial loss function of the first discriminator being used for measuring a difference degree between the predicted segmentation result of the target domain image and the predicted segmentation result of the source domain image.

20. The non-transitory storage medium according to claim 17, wherein, when the computer readable instructions cause the processor to train the second discriminator by using the predicted segmentation result of the source domain image and the standard segmentation result of the source domain image, the computer readable instructions cause the processor to:

respectively input the predicted segmentation result of the source domain image and the standard segmentation result of the source domain image to the second discriminator, to obtain a third discrimination result of the second discriminator for the predicted segmentation result of the source domain image and a fourth discrimination result of the second discriminator for the standard segmentation result of the source domain image;

calculate a value of a discrimination loss function of the second discriminator according to the third discrimination result and the fourth discrimination result, the discrimination loss function of the second discriminator being used for measuring a discrimination accuracy of the second discriminator; and adjust a parameter of the second discriminator by minimizing the value of the discrimination loss function of the second discriminator.

* * * * *